(12) United States Patent
Fukaya et al.

(10) Patent No.: US 6,222,372 B1
(45) Date of Patent: Apr. 24, 2001

(54) STRUCTURE OF GAS SENSOR

(75) Inventors: Kenji Fukaya, Chiryu; Masanobu Yamauchi, Kariya; Isao Watanabe; Hirokazu Yamada, both of Nagoya; Takashi Kojima, Kasugai, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/196,693

(22) Filed: Nov. 20, 1998

(30) Foreign Application Priority Data

Nov. 21, 1997 (JP) .................................................. 9-338084
Aug. 11, 1998 (JP) ................................................ 10-227225

(51) Int. Cl.[7] ........................... G01N 27/62; G01N 27/26
(52) U.S. Cl. ............................................ 324/464; 204/424
(58) Field of Search ..................... 324/464, 465, 324/468, 71.1; 204/424, 425, 427; 73/23.32

(56) References Cited

U.S. PATENT DOCUMENTS

| 4,123,131 | 10/1978 | Pearce, Jr. et al. . |
| 4,569,748 | 2/1986 | Yamakawa et al. . |
| 5,573,650 | * 11/1996 | Fukaya et al. ...................... 204/424 |
| 5,698,084 | * 12/1997 | Weyl et al. .......................... 204/424 |

FOREIGN PATENT DOCUMENTS

| 19703458 | 7/1997 | (DE) . |
| 0 899 562 | 3/1999 | (EP) . |
| 899562 | 3/1999 | (EP) . |
| 965838 | 12/1999 | (EP) . |
| 54-29090 | 3/1979 | (JP) . |
| 57-116246 | 7/1982 | (JP) . |
| 8-145939 | 6/1996 | (JP) . |
| 8-201338 | 8/1996 | (JP) . |
| 8-220061 | 8/1996 | (JP) . |
| 8-240559 | 9/1996 | (JP) . |

* cited by examiner

*Primary Examiner*—Safet Metjahic
*Assistant Examiner*—James C Kerveros
(74) *Attorney, Agent, or Firm*—Pillsbury Winthrop LLP

(57) ABSTRACT

A gas sensor measuring a given component content in a gas is provided which has an outer and an inner metallic cover, a sensing unit, and an insulator. The sensing unit consists of a measuring electrode to be exposed to the gas to be measured and a reference electrode to be exposed to a reference gas in a reference gas chamber. The measuring electrode and the reference electrode are disposed adjacent each other through a solid electrolyte body. The inner metallic cover is installed on an end of a sensor housing. The outer metallic cover is installed on the periphery of the inner metallic cover. The insulator is mounted within the inner metallic cover and has formed therein holes through which sensor signal pickup leads pass. The insulator has an outer wall different in geometry from an inner wall of the inner metallic cover to define a portion of a reference gas passage therebetween which leads to the reference gas chamber.

17 Claims, 10 Drawing Sheets

STRUCTURE OF GAS SENSOR

BACKGROUND OF THE INVENTION

1. Technical Field of the Invention

The present invention relates generally to an improvement on a gas sensor which may be employed in an oxygen measuring device of an air-fuel ratio control system measuring an oxygen content in exhaust gasses of an internal combustion engine of automotive vehicles.

2. Background of Related Art

For burning control of fuel in internal combustion engines of automotive vehicles, an air-fuel ratio sensor is installed in an exhaust system to measure an air-fuel ratio. Such an air-fuel ratio sensor is usually implemented with an oxygen sensor which has a pair of electrodes one of which is exposed to a gas to be measured and the other is exposed to a reference gas introduced into a reference gas chamber from the outside of the oxygen sensor.

In recent years, in order to improve installation of the oxygen sensor in the vehicle and decrease manufacturing costs thereof, the size of the oxygen sensor is required to be decreased. To this end, there has been proposed an improved structure in which the length of the oxygen sensor is shortened, and an outer cover or other parts are joined by crimping. The crimping, however, leads to a problem of reducing an area of a gas passage introducing the reference gas into the reference gas chamber, which will cause the flow of the reference gas to be lowered, resulting in a decrease in measuring accuracy.

SUMMARY OF THE INVENTION

It is therefore a principal object of the present invention to avoid the disadvantages of the prior art.

It is another object of the present invention to provide a compact structure of a gas sensor capable of measuring a given component content in gasses with desired accuracy.

According to one aspect of the present invention, there is provided a gas sensor measuring a given component content in a gas which comprises: (a) a housing; (b) a sensing unit having a given length, disposed in the housing, the sensing unit having defined in one end portion thereof a reference gas chamber to be filled with a reference gas and also having installed in the one end portion a measuring electrode to be exposed to the gas to be measured and a reference electrode to be exposed to the reference gas in the reference gas chamber, the measuring electrode and the reference electrode being disposed adjacent each other through a solid electrolyte body and providing through signal pickup leads sensor signals which are used in determining the given component content in the gas; (c) a first metallic cover installed on the housing to cover the other end portion of the sensing unit; (d) a second metallic cover installed on a periphery of the first metallic cover through a water-repellent filter, the second metallic cover being crimped to be joined to the first metallic cover through the water-repellent filter; (e) a first vent formed in the first metallic cover; (f) a second vent formed in the second metallic cover which communicates with the first vent through the water-repellent filter to introduce the reference gas into the reference gas chamber through a reference gas passage extending from the second vent to the reference gas chamber; and (g) an insulator mounted within the first metallic cover, having formed therein holes through which the signal pickup leads pass, the insulator having an outer wall different in geometry from an inner wall of the first metallic cover to define a portion of the reference gas passage between the outer wall of the insulator and the inner wall of the first metallic cover.

In the preferred mode of the invention, the portion of the reference gas passage faces the first vent of the first metallic cover.

The insulator is made of a cylindrical member. The portion of the reference gas passage defined between the outer wall of the insulator and the inner wall of the first metallic cover is determined in sectional area as a function of a maximum and minimum diameter of the insulator. A ratio of the minimum diameter to the maximum diameter is within a range of 0.8 to 0.95.

The outer wall of the insulator is of a polygonal shape which has either of flat surfaces and recessed surfaces each lying between adjacent two of vertexes so that the portion of the reference gas passage may include clearances between either of the flat surfaces and the recessed surfaces and the inner wall of the first metallic cover.

The outer wall of the insulator holder is of an octagonal shape.

The outer wall of the insulator has curved surfaces and either of flat surfaces and recessed surfaces each lying between adjacent two of the curved surfaces. The curved surfaces are opposed to each other so that the portion of the reference gas passages may include clearances between either of the flat surfaces and the recessed surfaces and the inner wall of the first metallic cover.

The outer wall of the insulator may be oval.

The second metallic cover has an opening through which the signal pickup leads extend to the outside of the second metallic cover. A sealing member is disposed in the second metallic cover to seal the opening and lies above the insulator with a clearance therebetween communicating with the portion of the reference gas passage between the outer wall of the insulator and the inner wall of the first metallic cover.

A spacer member may be disposed between the sealing member and the insulator to define the clearance communicating with the portion of the reference gas passage.

The sealing member may have a flange which is supported by ends of the first and second metallic covers.

The insulator may have a vent which defines a second portion of the reference gas passage.

The first metallic cover includes an outer cover member and an inner cover member. The outer cover member is so crimped to be joined to the inner cover member. The inner cover member has an end caulked to the housing.

According to the second aspect of the invention, there is provided a gas sensor measuring a given component content in a gas which comprises: (a) a housing; (b) a sensing unit having a given length, disposed in the housing, the sensing unit having defined in one end portion thereof a reference gas chamber to be filled with a reference gas and also having installed in the one end portion a measuring electrode to be exposed to the gas to be measured and a reference electrode to be exposed to the reference gas in the reference gas chamber, the measuring electrode and the reference electrode being disposed adjacent each other through a solid electrolyte body and providing through signal pickup leads sensor signals which are used in determining the given component content in the gas; (c) a first metallic cover having first and second ends, the first metallic cover being installed at the first end on the housing to cover the other end portion of the sensing unit and defining an opening in the second end; (d) a second metallic cover installed on a peripheral portion of the first metallic cover through a water-repellent filter, the second metallic cover being crimped to be joined to the first metallic cover through the water-repellent filter; (e) a first vent formed in the first metallic cover; (f) a second vent formed in the second metallic cover which communicates with the first vent through the water-repellent filter to introduce the reference gas into the reference gas chamber through a reference gas passage extending from the second vent to the reference gas chamber; (g) an insulator mounted within the first metallic cover, having formed therein holes through which the signal pickup leads pass; and (h) a sealing member sealing the opening defined in the second end of the first metallic cover, the sealing member having formed thereon a protrusion in contact with the insulator to define a gap between the sealing member and the insulator which occupies a portion of the reference gas passage.

In the preferred mode of the invention, the sealing member is disposed within the second end of the first metallic cover.

According to the third aspect of the invention, there is provided a gas sensor measuring a given component content in a gas which comprises: (a) a housing; (b) a sensing unit having a given length, disposed in the housing, the sensing unit having defined in one end portion thereof a reference gas chamber to be filled with a reference gas and also having installed in the one end portion a measuring electrode to be exposed to the gas to be measured and a reference electrode to be exposed to the reference gas in the reference gas chamber, the measuring electrode and the reference electrode being disposed adjacent each other through a solid electrolyte body and providing through signal pickup leads sensor signals which are used in determining the given component content in the gas; (c) a first metallic cover having first and second ends, the first metallic cover being installed at the first end on the housing to cover the other end portion of the sensing unit; (d) a second metallic cover installed on a periphery of the first metallic cover through a water-repellent filter, the second metallic cover being crimped to be joined to the first metallic cover through the water-repellent filter; (e) a first vent formed in the first metallic cover; (f) a second vent formed in the second metallic cover which communicates with the first vent through the water-repellent filter to introduce the reference gas into the reference gas chamber through a reference gas passage extending from the second vent to the reference gas chamber; (g) an insulator mounted within the first metallic cover, having formed therein holes through which the signal pickup leads pass; and (h) a sealing member having a flange which is supported by at least one of the first metallic cover and the second metallic cover to define a gap between the sealing member and the insulator which occupies a portion of the reference gas passage.

In the preferred mode of the invention, the sealing member has a first end and a second end opposite the first end. The flange is provided on the first end of the sealing member. The gap is defined between the second end of the sealing member and the insulator.

BRIEF DESCRIPTION OF THE DRAWINGS

The present invention will be understood more fully from the detailed description given hereinbelow and from the accompanying drawings of the preferred embodiment of the invention, which, however, should not be taken to limit the invention to the specific embodiment but are for explanation and understanding only.

In the drawings.

DESCRIPTION OF THE PREFERRED EMBODIMENT

Figure 1:
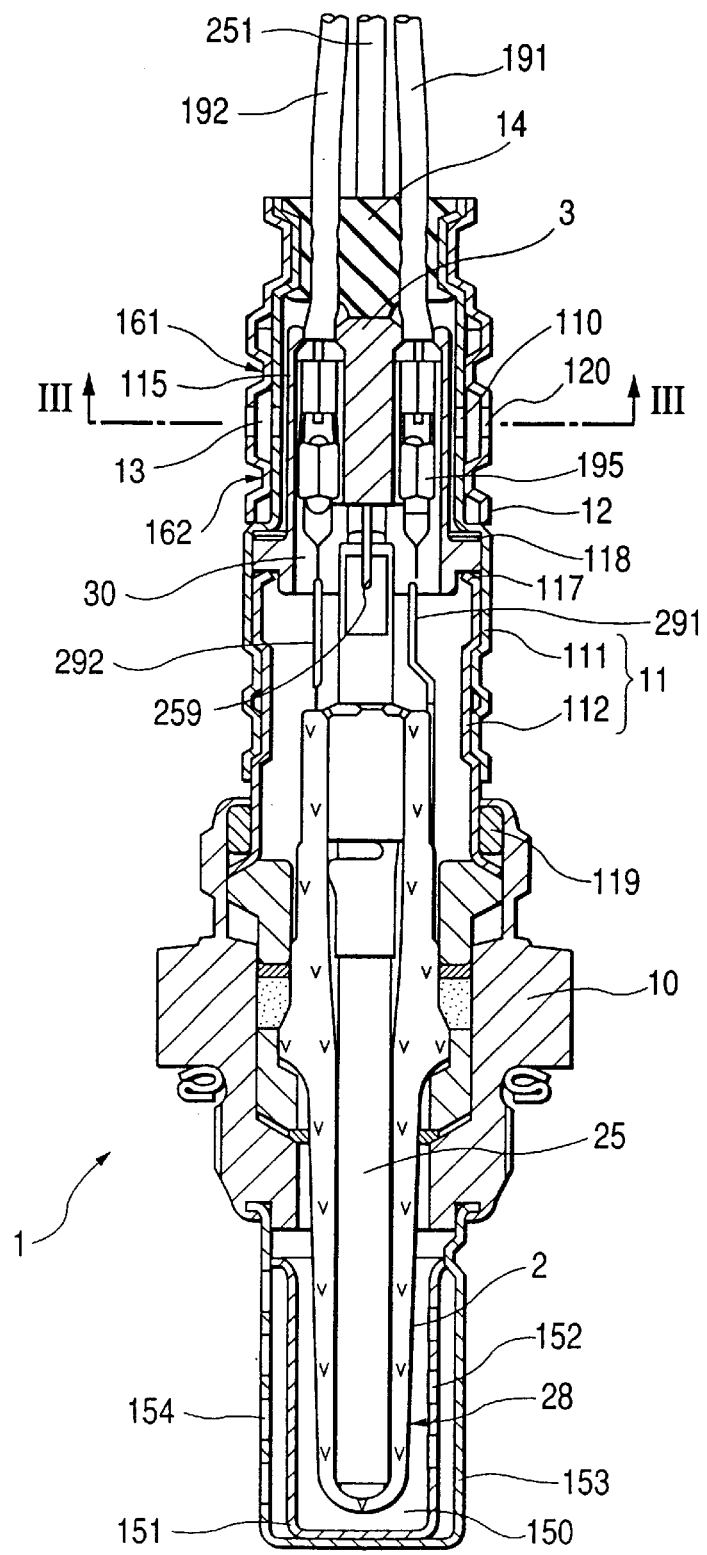
FIG. 1 is a longitudinal sectional view which shows an oxygen sensor according to the first embodiment of the invention.

Referring now to the drawings, particularly to FIG. 1, there is shown an oxygen sensor 1 according to the first embodiment of the invention which may be employed in an air-fuel ratio control system for automotive vehicles. Note that the present invention is not limited to an oxygen sensor and may alternatively be used with a variety of gas sensors such as HC, CO, and NOx sensors.

Figure 5:
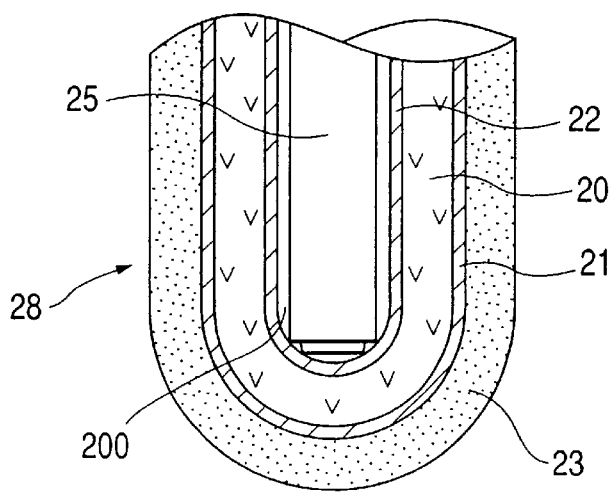
FIG. 5 is a partially sectional view which shows an arrangement of electrodes of the oxygen sensor in FIG. 1.

The oxygen sensor 1 generally includes a housing 10, a sensing unit 2, and signal pickup leads 291 and 292. The sensing unit 2 is disposed hermetically within the housing 10 and includes, as shown in FIG. 5, a sensing section 28 and a reference gas chamber 200. The sensing section 28 consists of a measuring electrode 21, a reference electrode 22, and a solid electrolyte body 20 interposed between the electrodes 21 and 22. The reference gas chamber 200 is filled with a reference gas to which the reference electrode 22 is exposed. The signal pickup leads 291 and 292 are electrically connected to the measuring electrode 21 and the reference electrode 292.

The oxygen sensor 1 also includes a first metallic cover 11 and a second metallic cover 12. The first metallic cover 11 covers a portion of the sensing unit 2 far from the sensing section 28 and is joined to the housing 10. The second metallic cover 12 is installed on the periphery of an upper portion of the first metallic cover 11 and is crimped to form two annular joints 161 and 162 to the first metallic cover 11 for retaining a water-repellent filter 13 between the first and second metallic covers 11 and 12.

First and second air vents 110 and 120 are formed in alignment in the first metallic cover 11 and the second metallic cover 12, respectively, which communicate with each other through the water-repellent filter 13 for introducing the reference gas into the reference gas chamber 200 through an upper end, as viewed in FIG. 1, of the sensing unit 2.

An insulating holder 3 is disposed inside the first metallic cover 11 through which the signal pickup leads 291 and 291 are inserted. The insulating holder 3 faces the first air vent 110 and is, as will be discussed later in detail, not contoured to an inner wall of the first metallic cover 11 to define a reference gas passage 115 therebetween.

The sensing unit 2 is retained within the housing 10. The sensing unit 2 and the housing 10 are hermetically sealed.

The housing 10 has disposed on the head thereof cap-shaped inner and outer covers 151 and 153 which cover the sensing section 28. The inner cover 151 defines therein a gas-measuring chamber 150. Gas inlets 152 and 154 are formed in the inner and outer covers 151 and 153, respectively.

The first metallic cover 11 consists of two cover members: outer and inner cover members 111 and 112. The inner cover member 112 is joined at an end to an upper end of the housing 10 through a caulking ring 119. The outer cover member 111 is joined to an upper portion of the inner cover member 112 by crimping.

The inner cover member 112 has an upper end 117 which cramps a lower flange of the insulating holder 3 between itself and a shoulder 118 of the outer cover member 111 to retain the insulating holder 3 within the outer cover member 111. A sealing member 14 is fitted in an upper end of the inner cover member 112 in contact with the upper end of the insulating holder 3. The leads 191, 192, and 251 pass through the sealing member 14.

The insulating holder 3 has formed therein four through holes 30 through which the signal pickup leads 291 and 292, a pair of leads 259 connected to a heater 25, as will be described later in detail, the leads 191 and 192, and a pair of leads 251 pass. The leads 291, 292, and 259 are connected to the leads 191, 192, and 251 within the through holes 30, respectively.

Figure 3:
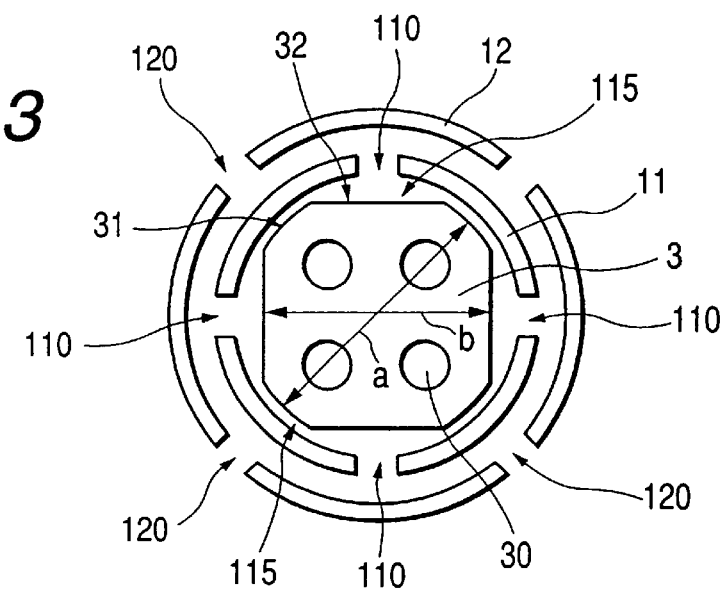
FIG. 3 is a traverse sectional view taken along the line III—III in FIG. 1.

The insulating holder 3 is, as clearly shown in FIG. 3, of substantially an octagonal configuration. Specifically, the insulating holder 3 has rounded or curved surfaces 31 at corners thereof.

Each of the through holes 30 is located close to one of the curved surfaces 31. The insulating holder 3 has flat passage surfaces 32 each defined between adjacent two of the curved surfaces 31 to form a major portion of the reference gas passage 115.

If the distance between opposed two of the curved surfaces 31 of the insulating holder 3 (i.e., a maximum length) is defined as a, and the distance between opposed two of the flat passage surfaces 32 (i.e., a minimum length) is defined as b, it is advisable that a ratio of b to a (i.e., b/a) be greater than or equal to 0.8 and smaller than or equal to 0.95 (0.8<b/a<0.95). When the ratio of b to a is smaller than 0.8, it will become difficult to ensure a desired diameter of the four through holes 30. Alternatively, when the ratio of b to a is greater than 0.95, the clearance between the insulating holder 3 and the first metallic cover 11 becomes too small to ensure a sufficient flow of the reference gas.

Figure 4:
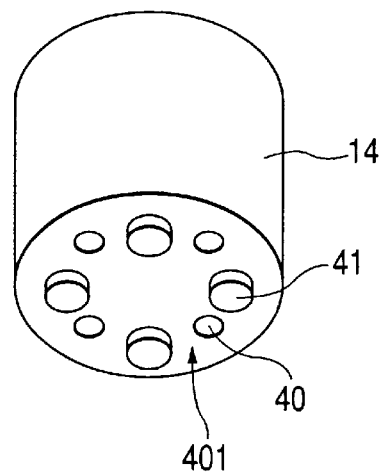
FIG. 4 is a perspective view which sows a sealing member disposed within the oxygen sensor in FIG. 1.

The sealing member 14 is, as clearly shown in FIG. 4, cylindrical and has formed on an end surface 410 facing the insulating holder 3 a plurality (four in this embodiment) of protrusions 41 which contact with the upper surface of the insulating holder 3, as can be seen in FIG. 1, to keep a gap therebetween through which the reference gas is allowed to flow. The sealing member 14 also has formed therein four through holes 40 each of which lies between adjacent two of the protrusions 41 and through which the leads 191, 192, and 252 pass.

The second metallic cover 12 is crimped to form the annular joints 161 and 162 so that it is attached to the outer cover member 111 of the first metallic cover through the water-repellent filter 13.

The sensing unit 2, as shown in FIG. 5, consists of the hollow cylindrical solid electrolyte body 20 with a bottom, the measuring electrode 21 exposed to the gas chamber 150 through a protective layer 23, and the reference electrode 22 exposed to the reference gas chamber 200. Within the reference gas chamber 200, the bar-shaped heater 25 is disposed which heats the measuring electrode 21 and the reference electrode 22 up to a temperature at which the oxygen concentration is allowed to be measured correctly.

The measuring electrode 21 and the reference electrode 22 extend to an upper portion, as viewed in FIG. 1, of the sensing unit 2 and connect with the signal pickup leads 291 and 292. The heater 25 has disposed therein a heating resistor connected to the leads 259.

Figure 6A:
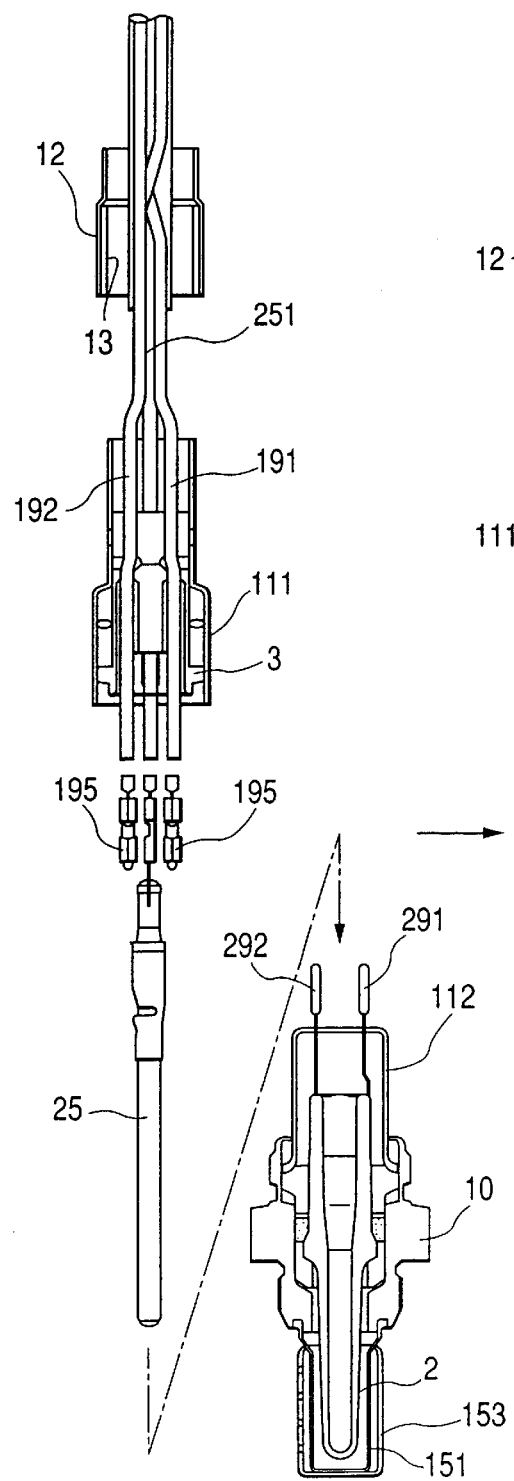
FIGS. 6(a), 6(b), and 6(c) shows a sequence of assembling processes of the oxygen sensor in FIG. 1.

In assembly of the oxygen sensor 1, the sensing unit 2, as shown in FIG. 6(a), to which the signal pickup leads 291 and 292 is connected is first inserted into the housing 10 hermetically. The inner and outer covers 151 and 153 are installed on the lower end of the housing 10. The inner cover member 112 of the first metallic cover 11 is staked so that it is joined to the upper end of the housing 10. This completes a lower portion of the oxygen sensor 1.

The leads 191, 192, and 251 are, as shown in FIG. 6(a), inserted into the insulating holder 3. The outer cover member 111 of the first metallic cover 11 is installed on the periphery of the insulating holder 3. To the leads 251, the leads 259 of the heater 25 are connected through connectors 195. The second metallic cover 12 with the water-repellent filter 13 is arranged above the outer cover member 111.

Figure 6B:
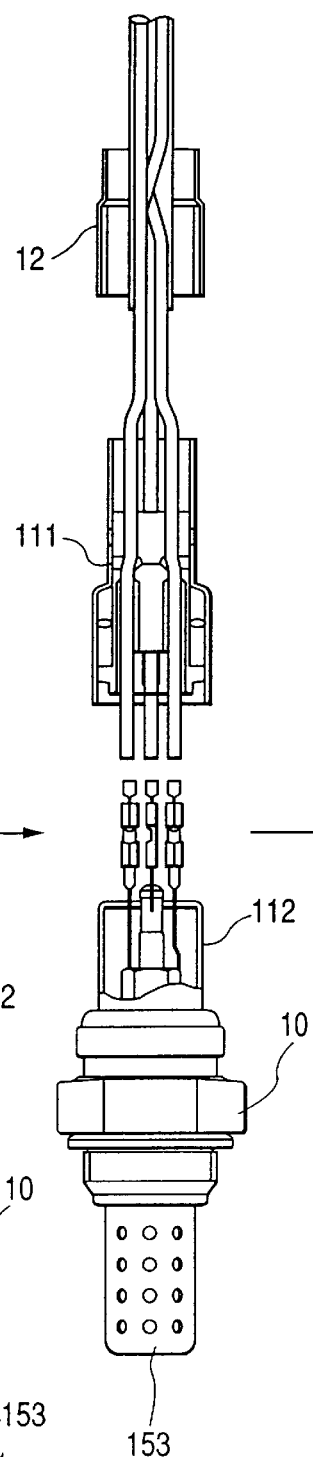

Next, the connectors 195 are, as shown in FIG. 6(b), joined to the signal pickup leads 291 and 292. The outer cover member 111 is put on the inner cover member 112 and then crimped to be joined thereto to complete the first metallic cover 11.

Figure 6C:
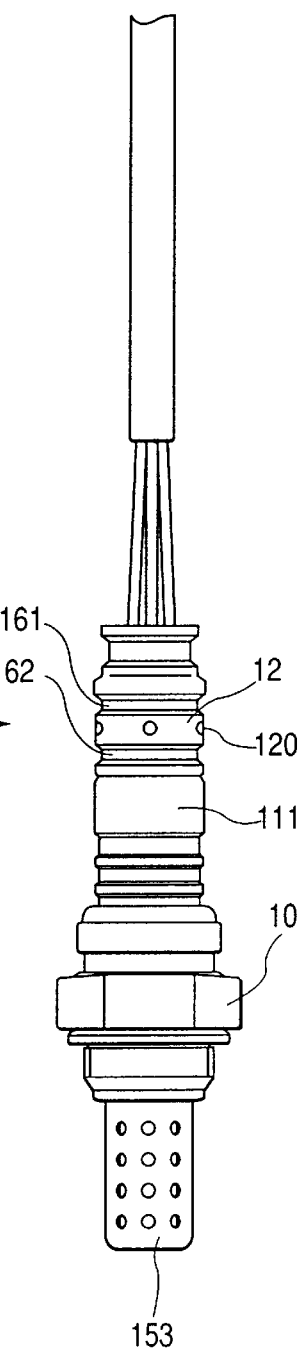

The second metallic cover 12 is put on the first metallic cover 11 and crimped to form the annular joints 161 and 162. This complete the oxygen sensor 1, as shown in FIG. 6(c).

Figure 2:
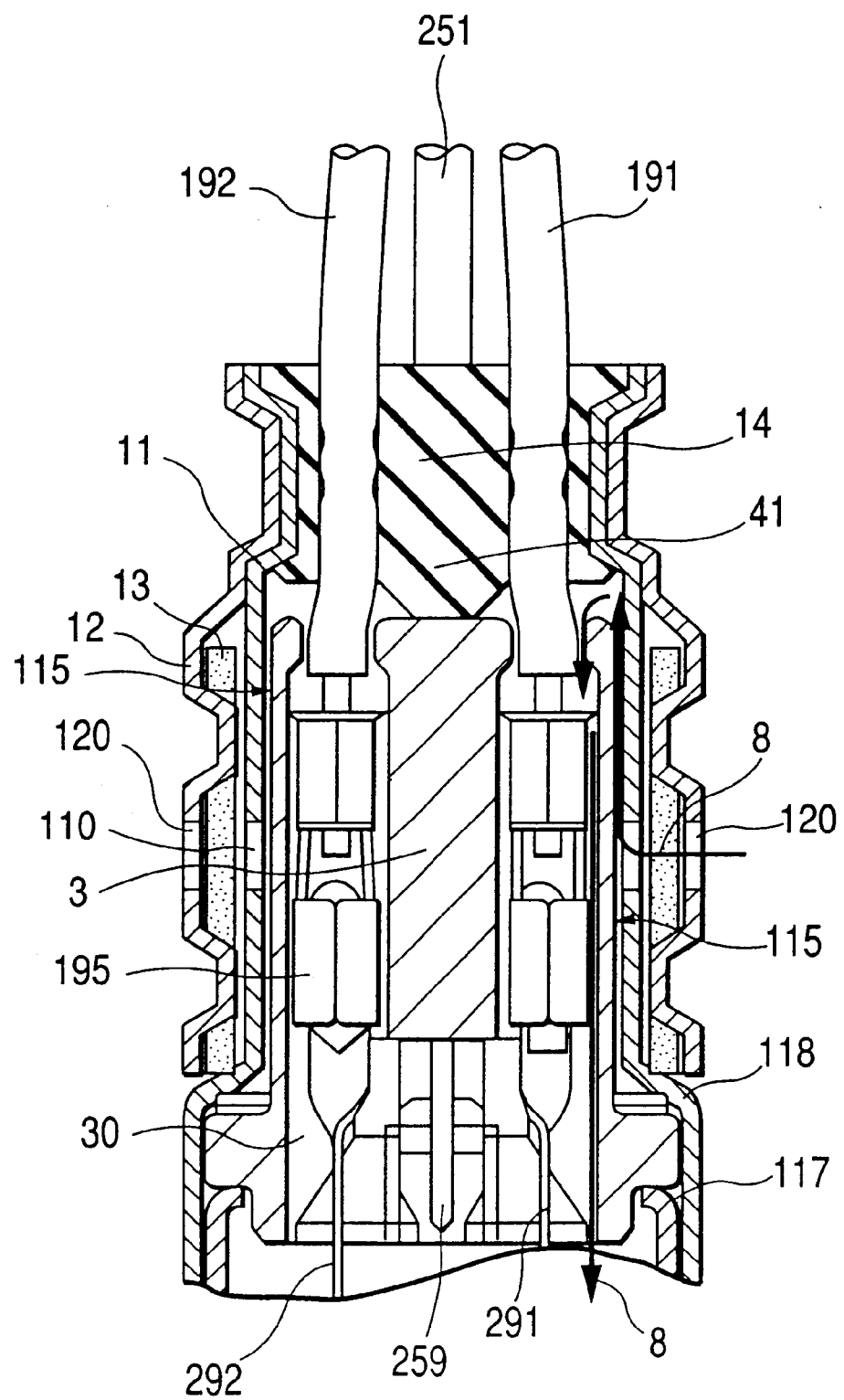
FIG. 2 is a partially exploded view which shows the oxygen sensor in FIG. 1.

In operation, air 8, as shown in FIG. 2, is first introduced from the second air vent 120 to the first air vent 110 through the water-repellent filter 13 and then flows through the reference gas passage 115 formed between the periphery of the insulating holder 3 and the inner wall of the first metallic cover 11 upward and reaches the upper edge of the insulating holder 3. Next, the air 8 passes through the gap between the insulating holder 3 and the sealing member 14 and flows downward through clearances between the leads 191, 192, and 251 and the inner walls of the holes 30 formed in the insulating holder 3. The air 8 emerging from the lower ends of the holes 30 enter the reference gas chamber 200 at the upper end of the sensing unit 2.

The oxygen sensor 1 of this invention is designed to measure an oxygen content in gases using the oxygen concentration dependent electromotive force or the limiting current. Specifically, the measurement of the oxygen content using the oxygen concentration dependent electromotive force is accomplished by monitoring through the measuring electrode 21 and the reference electrode 22 the electromotive force produced in the solid electrolyte body 20 which depends upon a difference in oxygen concentration between the air 8 (i.e., a reference gas) and the gas within the gas-measuring chamber 150. The measurement of the oxygen content using the limiting current is accomplished by applying a given voltage across the measuring electrode 21 and the reference electrode 22 to pick up a limiting current which depends upon the concentration of oxygen in the gasses. These techniques are known in the art, and explanation thereof in detail will be omitted here.

Figure 7:
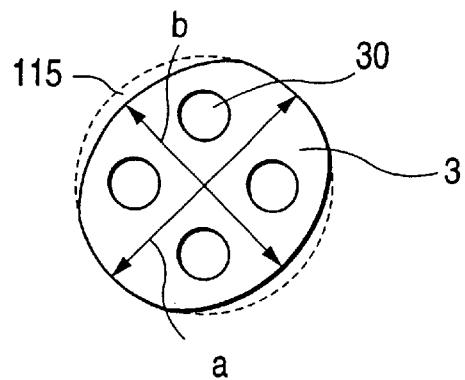
FIG. 7 is a plan view which shows the first modification of an insulating holder disposed within an oxygen sensor.

FIG. 7 shows the first modification of the insulating holder 3 which has an oval shape having a major axis a and a minor axis b to define two major portions of the reference gas passage 115 between the insulating holder 3 and the first metallic cover 11. The ratio of b to a is, like the one shown in FIG. 3, within a range from 0.8 to 0.95.

Figure 8:
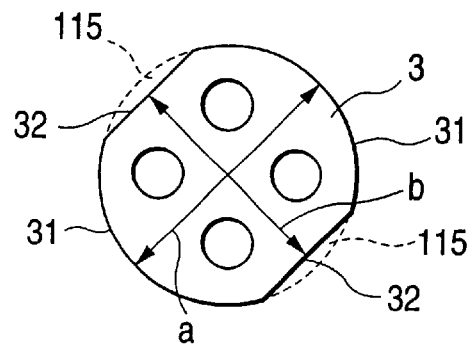
FIG. 8 is a plan view which shows the second modification of an insulating holder disposed within an oxygen sensor.

FIG. 8 shows the second modification of the insulating holder 3 which is made of a cylindrical member with two flat surfaces 32 defining two major portions of the reference gas passage 115 between the insulating holder 3 and the first metallic cover 11. The ratio of b to a is, like the above, within a range from 0.8 to 0.95.

Figure 9:
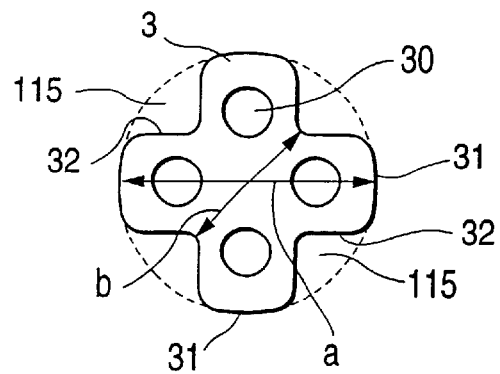
FIG. 9 is a plan view which shows the third modification of an insulating holder disposed within an oxygen sensor.

FIG. 9 shows the third modification of the insulating holder 3 which has a cruciate shape in cross section defining four major portions of the reference gas passage 115 between L-shaped surfaces 32 and the outer cover member 111 of the first metallic cover 11. The ratio of b to a is, like the above, within a range from 0.8 to 0.95.

Figure 10:
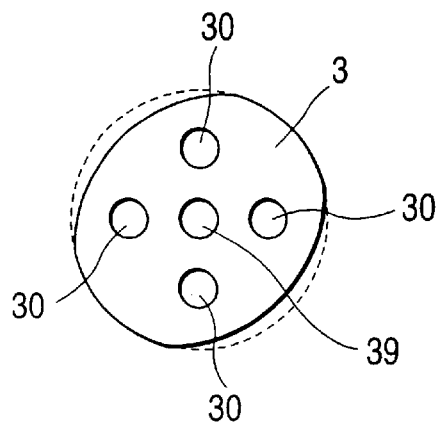
FIG. 10 is a plan view which shows the fourth modification of an insulating holder disposed within an oxygen sensor.

FIG. 10 shows the fourth modification of the insulating holder 3 which has formed therein a central through hole 39 which direct the air 8 reaching the upper end of the insulating holder 3 to the upper end of the sensing unit 2. The insulating holder 3 is illustrated as having the shape similar to the one shown in FIG. 7, but may have any of the shapes shown in FIGS. 3, 8, and 9.

Figure 11:
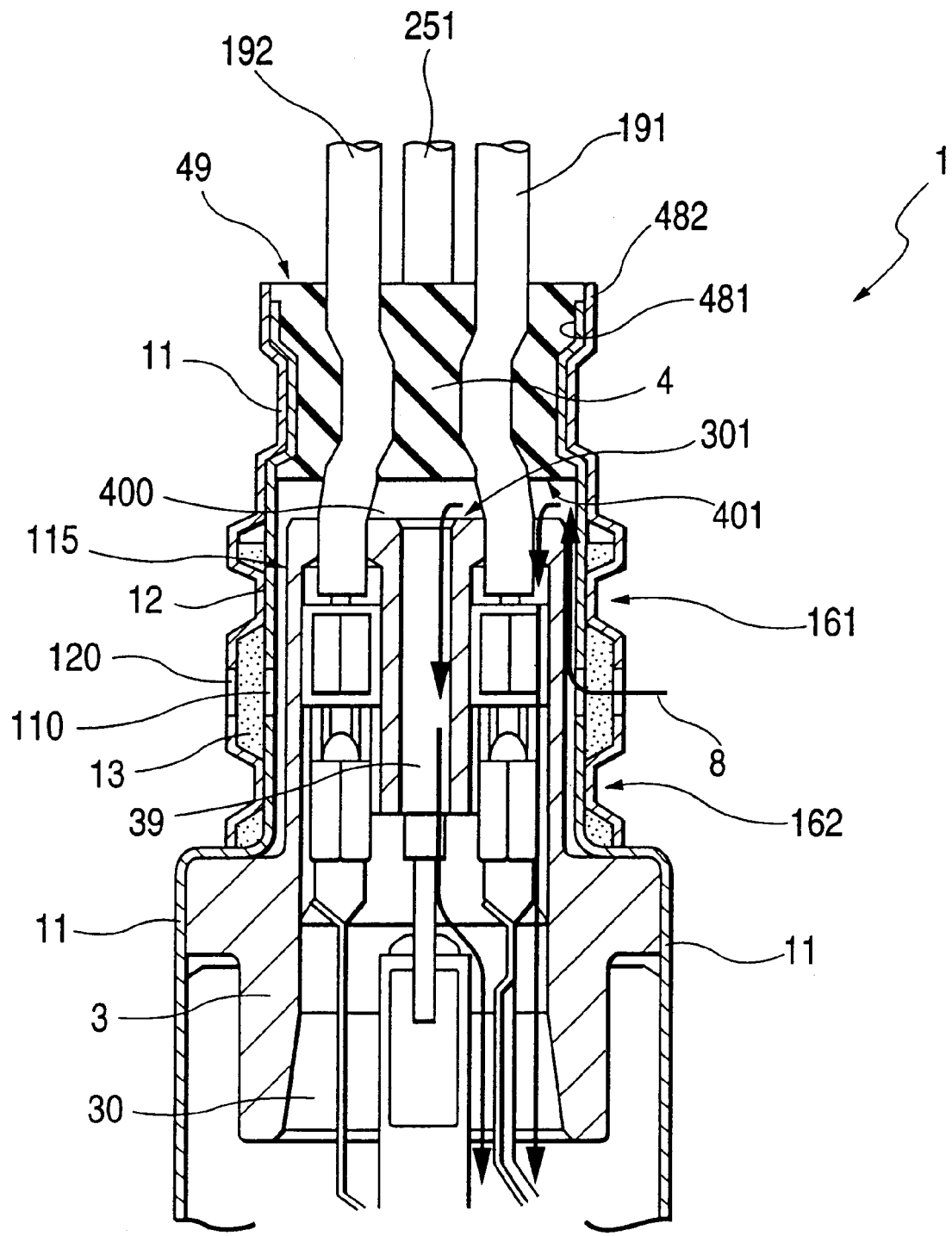
FIG. 11 is a partially sectional view which shows the second embodiment of an oxygen sensor according to the present invention.

FIG. 11 shows the second embodiment of the oxygen sensor 1.

Figure 12:
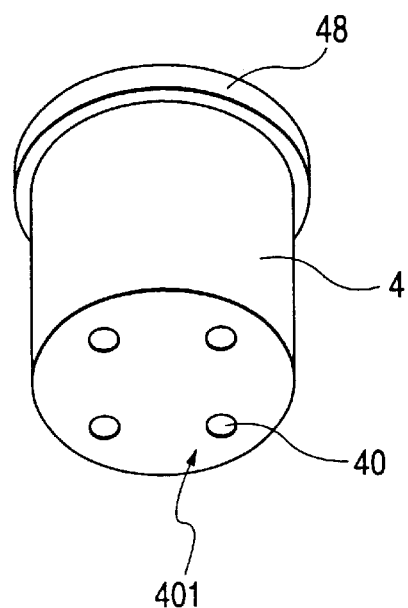
FIG. 12 is a perspective view which shows a sealing member of the oxygen sensor in FIG. 11.
Figure 13:
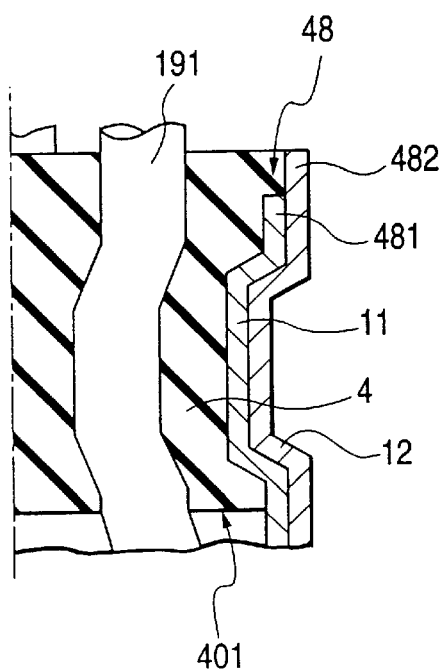
FIG. 13 is a partially sectional view which shows the sealing member in FIG. 12 retained on an end of a first metallic cover.

The sealing member 4, as shown in FIG. 12, has a flange 48 on an upper end thereof and four curved holes 40 through which leads 191, 192, and 252 pass. The curving of the holes 40 serves to hold the leads 191, 192, and 252 in the sealing member 4 firmly. The first metallic cover 11 has, as clearly shown in FIG. 13, an end portion 481 shorter than an end portion 482 of the second metallic cover 12 to form an annular step on which the flange 48 of the sealing member 4 is retained, thereby defining a constant gas between the bottom 401 of the sealing member 4 and the upper surface 400 of the insulating holder 3.

Figure 14:
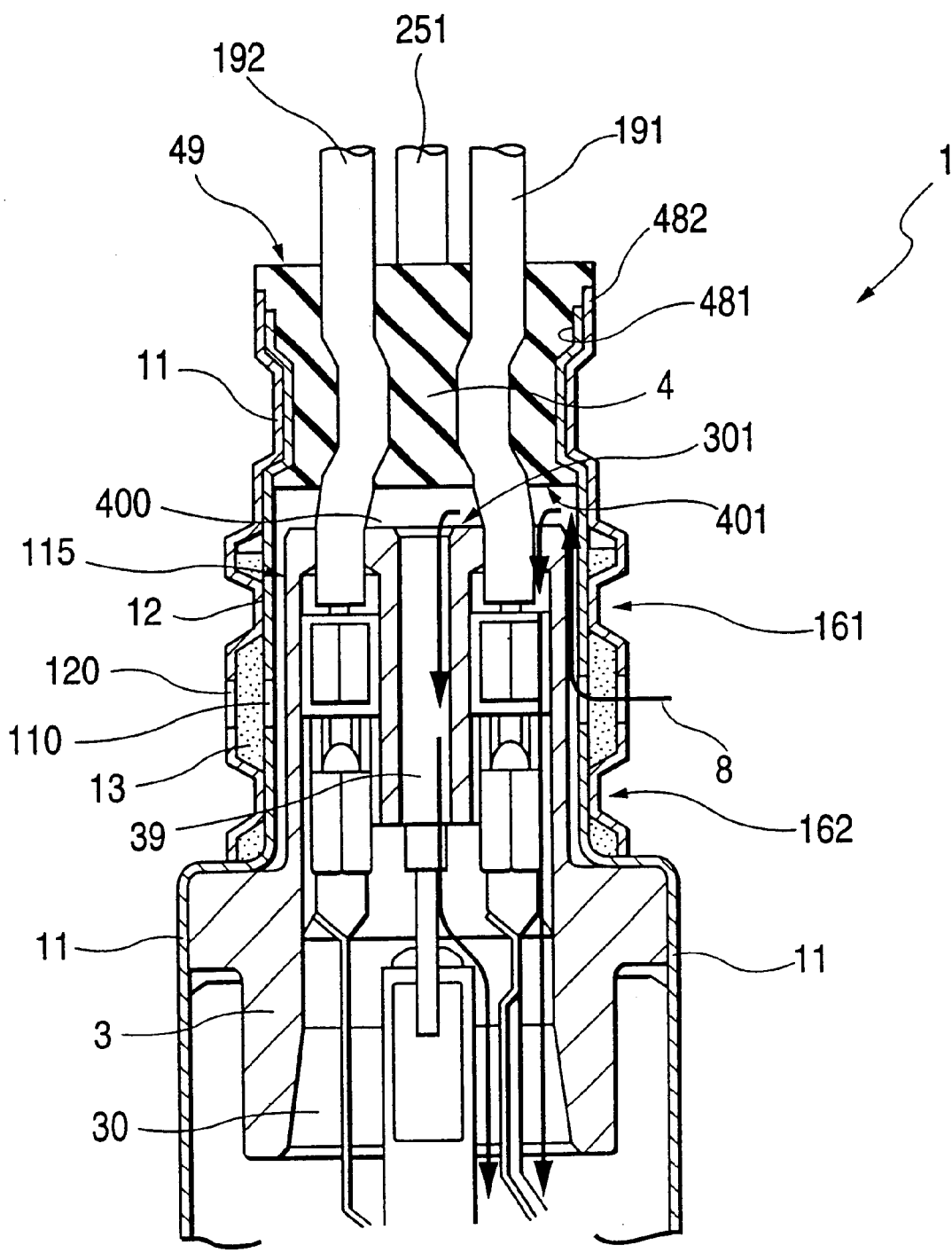
FIG. 14 is a partially sectional view which shows a modification of the second embodiment in FIG. 11.

The sealing member 4 may alternatively have an additional flange 49, as shown in FIG. 14, formed on the upper end thereof which is retained on the end of the second metallic cover 12 to define the constant gap between the bottom 401 of the sealing member 4 and the upper surface 400 of the insulating holder 3.

Figure 15:
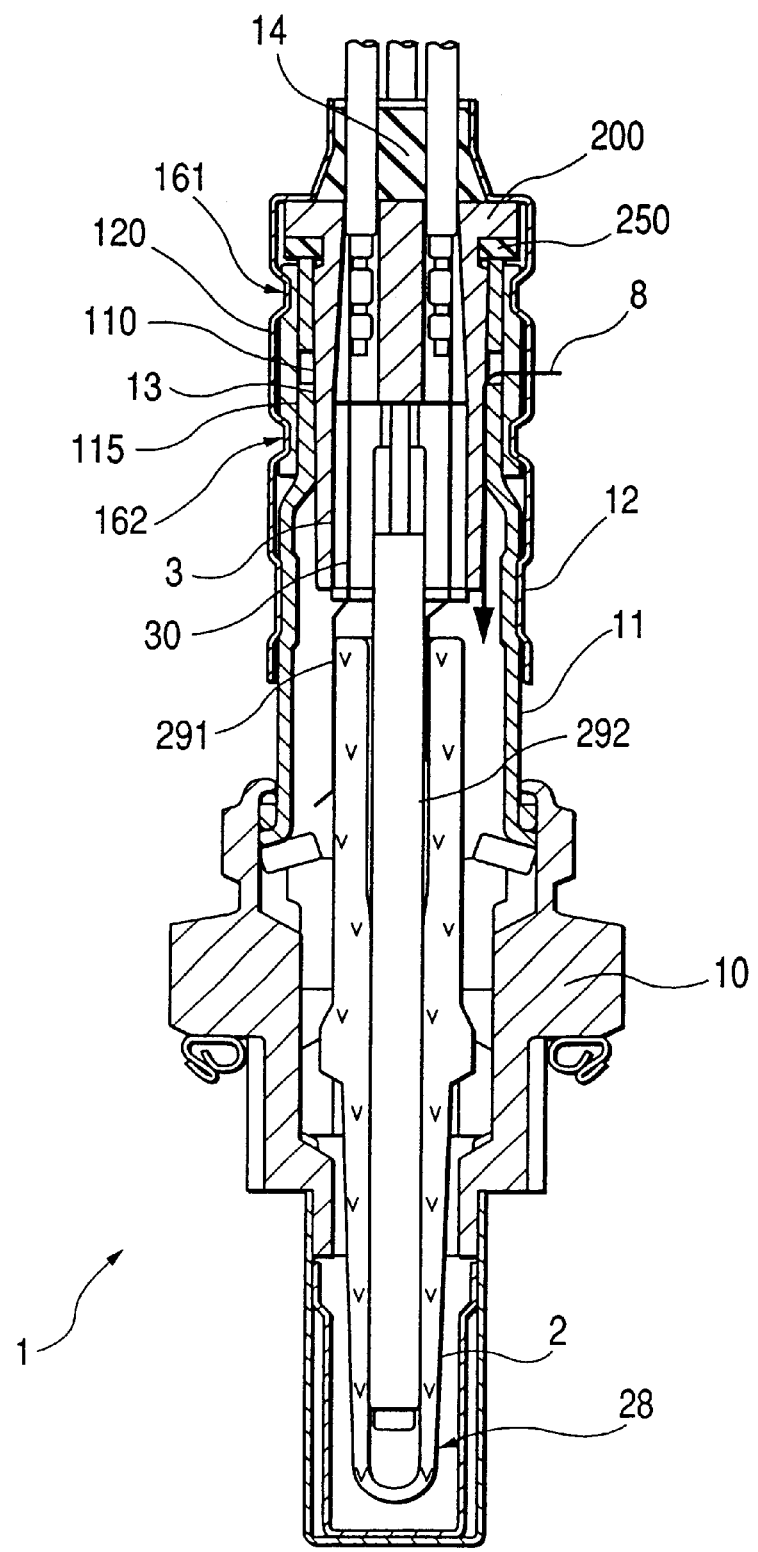
FIG. 15 is a longitudinal sectional view which shows an oxygen sensor according to the third embodiment of the invention.

FIG. 15 shows the third embodiment of the oxygen sensor 1 which includes the first metallic cover 11 made of a single cylindrical member. The sealing member 14 is disposed on the insulating holder 3 with almost no clearances. The insulating holder 3 has an upper flange 200 and a hollow body whose peripheral wall is similar in shape with any one of the insulating holders 3 in FIGS. 3, 7, 8, and 9. The upper flange 200 is supported on an upper end of the first metallic cover 1 1 through a rubber-made packing 250.

The air 8 which is sucked from the second air vent 120 through the water-repellent filter 13 and the first vent 110 flows through the reference gas passage 115 downward and then enters the reference gas chamber 20 at the upper end of the sensing unit 2.

Figure 16:
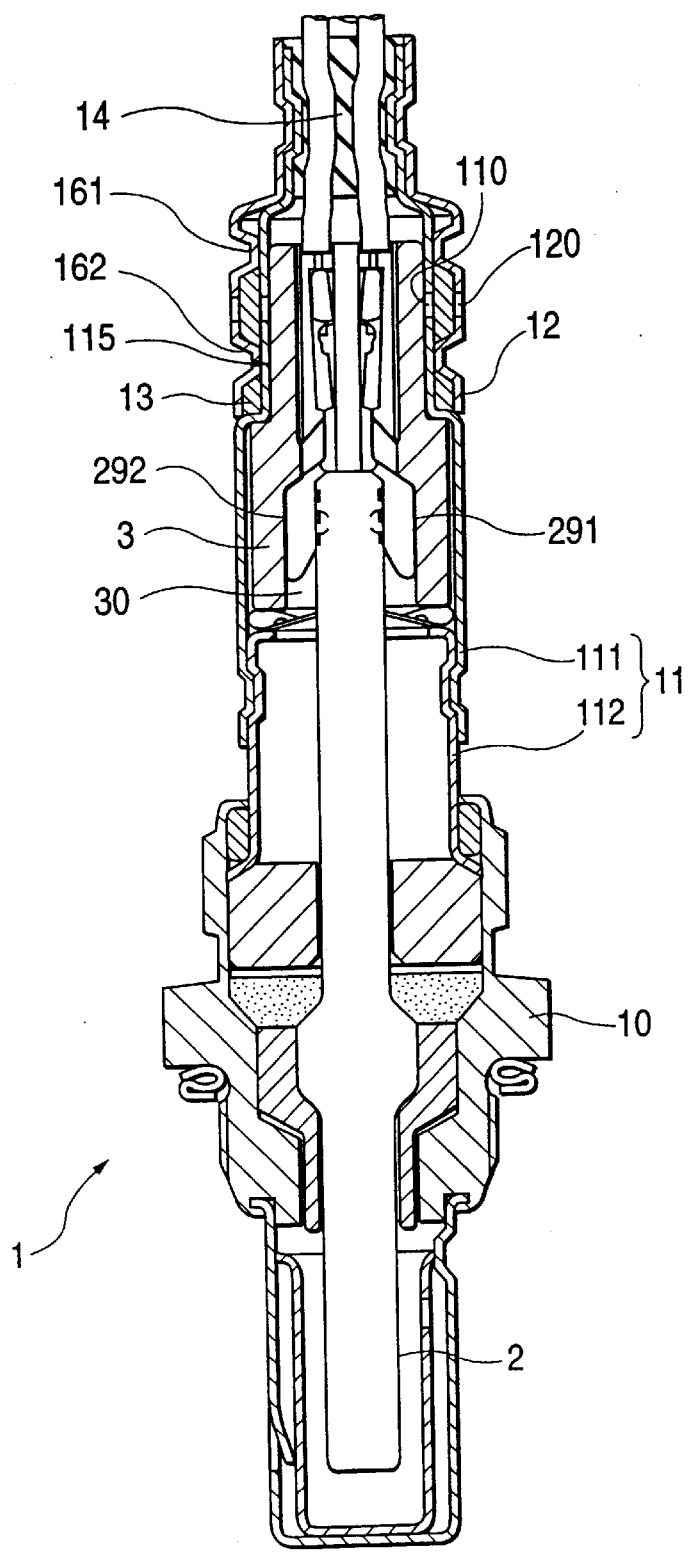
FIG. 16 is a longitudinal sectional view which shows an oxygen sensor according to the fourth embodiment of the invention.

FIG. 16 shows the fourth embodiment of the oxygen sensor 1 which includes a sensing unit 2 formed with laminations. For example, U.S. Pat. No. 5,573,650, issued Nov. 12, 1996 to Fukaya et al., teaches such a structure of the sensing unit 2, disclosure of which is incorporated herein by reference.

While the present invention has been disclosed in terms of the preferred embodiment in order to facilitate a better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A gas sensor measuring a given component content in a gas comprising:

a housing;

a sensing unit having a given length, disposed in said housing, said sensing unit having defined in one end portion thereof a reference gas chamber to be filled with a reference gas and also having installed in the one end portion a measuring electrode to be exposed to the gas to be measured and a reference electrode to be exposed to the reference gas in the reference gas chamber, the measuring electrode and the reference electrode being disposed adjacent to each other through a solid electrolyte body and providing through signal pickup leads sensor signals which are used in determining the given component content in the gas;

a first metallic cover installed on said housing to cover the other end portion of said sensing unit;

a second metallic cover installed on a periphery of said first metallic cover through a water-repellent filter, said second metallic cover being crimped to be joined to said first metallic cover through the water-repellent filter;

a first vent formed in said first metallic cover;

a second vent formed in said second metallic cover which communicates with said first vent through the water-repellent filter to introduce the reference gas into the reference gas chamber through a reference gas passage extending from said second vent to the reference gas chamber; and an insulator mounted within said first metallic cover, having formed therein holes through which the signal pickup leads pass, said insulator having an outer wall different in geometry from an inner wall of said first metallic cover to define a portion of the reference gas passage between the outer wall of said insulator and the inner wall of said first metallic cover, wherein the different in geometry of the outer wall of said insulator from the inner wall of said first metallic cover provides better flow of the reference gas into the reference gas chamber.

2. A gas sensor as set forth in claim 1, wherein said portion of the reference gas passage faces the first vent of said first metallic cover.

3. A gas sensor as set forth in claim 1, wherein said insulator is made of a cylindrical member, and wherein said portion of the reference gas passage defined between the outer wall of said insulator and the inner wall of said first metallic cover is determined in sectional area as a function of a maximum and minimum diameter of said insulator, a ratio of the minimum diameter to the maximum diameter being within a range of 0.8 to 0.95.

4. A gas sensor as set forth in claim 1, wherein the outer wall of said insulator is of a polygonal shape which has either of flat surfaces and recessed surfaces each lying between adjacent two of vertexes so that said portion of the reference gas passage includes clearances between either of the flat surfaces and the recessed surfaces and the inner wall of said first metallic cover.

5. A gas sensor as set forth in claim 4, wherein the outer wall of said insulator holder is of an octagonal shape.

6. A gas sensor as set forth in claim 1, wherein the outer wall of said insulator has curved surfaces and either of flat surfaces and recessed surfaces each lying between adjacent two of the curved surfaces, the curved surfaces being opposed to each other so that said portion of the reference gas passages includes clearances between either of the flat surfaces and the recessed surfaces and the inner wall of said first metallic cover.

7. A gas sensor as set forth in claim 1, wherein the outer wall of said insulator is oval.

8. A gas sensor as set forth in claim 1, wherein said second metallic cover has an opening through which the signal pickup leads extend to the outside of said second metallic cover, and further including a sealing member disposed in said second metallic cover to seal the opening, said sealing member lying above said insulator with a clearance therebetween communicating with said portion of the reference gas passage between the outer wall of said insulator and the inner wall of said first metallic cover.

9. A gas sensor as set forth in claim 8, further including a spacer member disposed between said sealing member and said insulator to define the clearance communicating with said portion of the reference gas passage.

10. A gas sensor as set forth in claim 8, wherein said sealing member has a flange which is supported by ends of said first and second metallic covers.

11. A gas sensor as set forth in claim 1, wherein said insulator has a vent which defines a second portion of the reference gas passage.

12. A gas sensor as set forth in claim 1, wherein said first metallic cover includes an outer cover member and an inner cover member.

13. A gas sensor as set forth in claim 12, wherein the outer cover member is so crimped to be joined to the inner cover member, and wherein the inner cover member has an end caulked to said housing.

14. A gas sensor measuring a given component content in a gas comprising:

a housing;

a sensing unit having a given length, disposed in said housing, said sensing unit having defined in one end portion thereof a reference gas chamber to be filled with a reference gas and also having installed in the one end portion a measuring electrode to be exposed to the gas to be measured and a reference electrode to be exposed to the reference gas in the reference gas chamber, the measuring electrode and the reference electrode being disposed adjacent to each other through a solid electrolyte body and providing through signal pickup leads sensor signals which are used in determining the given component content in the gas;

a first metallic cover having first and second ends, said first metallic cover being installed at the first end on said housing to cover the other end portion of said sensing unit and defining an opening in the second end;

a second metallic cover installed on a peripheral portion of said first metallic cover through a water-repellent filter, said second metallic cover being crimped to be joined to said first metallic cover through the water-repellent filter;

a first vent formed in said first metallic cover;

a second vent formed in said second metallic cover which communicates with said first vent through the water-repellent filter to introduce the reference gas into the reference gas chamber through a reference gas passage extending from said second vent to the reference gas chamber;

an insulator mounted within said first metallic cover, having formed therein holes through which the signal pickup leads pass, said insulator having an outer wall different in geometry from an inner wall of said first metallic cover; and a sealing member sealing the opening defined in the second end of said first metallic cover, said sealing member having formed thereon a protrusion in contact with said insulator to define a gap between said sealing member and said insulator which occupies a portion of the reference gas passage, wherein the different in geometry of the outer wall of said insulator from the inner wall of said first metallic cover provides better flow of the reference gas into the reference gas chamber.

15. A gas sensor as set forth in claim 14, wherein said sealing member is disposed within the second end of said first metallic cover.

16. A gas sensor measuring a given component content in a gas comprising:

a housing;

a sensing unit having a given length, disposed in said housing, said sensing unit having defined in one end portion thereof a reference gas chamber to be filled with a reference gas and also having installed in the one end portion a measuring electrode to be exposed to the gas to be measured and a reference electrode to be exposed to the reference gas in the reference gas chamber, the measuring electrode and the reference electrode being disposed adjacent to each other through a solid electrolyte body and providing through signal pickup leads sensor signals which are used in determining the given component content in the gas;

a first metallic cover having first and second ends, said first metallic cover being installed at the first end on said housing to cover the other end portion of said sensing unit;

a second metallic cover installed on a periphery of said first metallic cover through a water-repellent filter, said second metallic cover being crimped to be joined to said first metallic cover through the water-repellent filter;

a first vent formed in said first metallic cover;

a second vent formed in said second metallic cover which communicates with said first vent through the water-repellent filter to introduce the reference gas into the reference gas chamber through a reference gas passage extending from said second vent to the reference gas chamber;

an insulator mounted within said first metallic cover, having formed therein holes through which the signal pickup leads pass, said insulator having an outer wall different in geometry from an inner wall of said first metallic cover; and a sealing member having a flange which is supported by at least one of said first metallic cover and said second metallic cover to define a gap between said sealing member and said insulator which occupies a portion of the reference gas passage, wherein the different in geometry of the outer wall of said insulator from the inner wall of said first metallic cover provides better flow of the reference gas into the reference gas chamber.

17. A gas sensor as set forth in claim 16, wherein said sealing member has a first end and a second end opposite the first end, the flange being provided on the first end of said sealing member, the gap being defined between the second end of said sealing member and said insulator.

* * * * *